US006638935B2

(12) United States Patent
Emig et al.

(10) Patent No.: US 6,638,935 B2
(45) Date of Patent: Oct. 28, 2003

(54) HETEROARY1 DERIVATIVES AND THEIR USE AS MEDICAMENTS

(75) Inventors: Peter Emig, Bruchköbel (DE); Eckhard Günther, Maintal (DE); Bernhard Kutscher, Maintal (DE); Bernd Nickel, Mühltal (DE); Jürgen Schmidt, Uhldingen-Mühlhofen (DE); Anita Storch, Dietzenbach (DE)

(73) Assignee: Zentaris AG, Frankfurt (DE)

( * ) Notice: Subject to any disclaimer, the term of this patent is extended or adjusted under 35 U.S.C. 154(b) by 0 days.

(21) Appl. No.: 09/910,139

(22) Filed: Jul. 20, 2001

(65) Prior Publication Data
US 2002/0111354 A1 Aug. 15, 2002

(30) Foreign Application Priority Data
Jul. 21, 2000 (DE) .......................................... 100 35 908

(51) Int. Cl.$^7$ ..................... A61K 31/496; C07D 401/06
(52) U.S. Cl. ............................. 514/252.11; 514/252.18; 514/253.03; 514/253.06; 514/253.09; 514/253.1; 514/253.11; 514/253.13; 544/295; 544/357; 544/361; 544/364; 544/365
(58) Field of Search ............................ 514/337, 252.13, 514/357, 252.14, 314, 253.05, 233.06, 252.11, 252.18, 253.03, 253.06, 253.09, 253.1, 253.11, 253.13; 546/314, 318, 329, 339; 544/359, 380, 361, 363, 204, 295, 357, 364, 365

(56) References Cited

U.S. PATENT DOCUMENTS 4,937,246 A * 6/1990 Sugihara et al. ....... 514/254.11

FOREIGN PATENT DOCUMENTS

| DE | 2 215 1545 | 10/1972 |
|----|------------|---------|
| DE | 2 240 665 | 3/1974 |
| DE | 28 28 888 | 1/1979 |
| EP | 0 040 793 A1 | 12/1981 |
| EP | 0 318 235 A2 | 5/1989 |
| EP | 0 350 448 A1 | 1/1990 |
| EP | 1 006 110 A1 | 6/2000 |
| WO | WO 95/00497 | 1/1995 |
| WO | WO 96/21648 | 7/1996 |
| WO | WO 96/28427 | 9/1996 |
| WO | WO 98/00402 | 1/1998 |
| WO | WO 99/43682 | 9/1999 |
| WO | WO 00/52001 | 9/2000 |
| WO | WO 00/76521 A1 | 12/2000 |
| WO | WO 01/44201 A1 | 6/2001 |

OTHER PUBLICATIONS

Simone,"Oncology";Cecil Textbook of Medicine,section 154,pp. 1004–1010(1996).*
6001 Chemical Abstracts, Columbus, OH, US, vol. 68, 00–00–1968 XP–002185958.
6001 Chemical Abstracts, Columbus, OH, US, vol. 84, Jun. 21, 1976, No. 25 XP–002185954.
6001 Chemical Abstracts, Columbus, OH, US, vol. 94, 00–00–1981 XP–002185959.
6001 Chemical Abstracts, Columbus, OH, US, vol. 95, 00–00–1981 XP–002185957.
6001 Chemical Abstracts, Columbus, OH, US, vol. 104, 00–00–1986 XP–002185956.
6001 Chemical Abstracts, Columbus, OH, US, vol. 134 XP–002185955.

* cited by examiner

*Primary Examiner*—Richard L. Raymond
(74) *Attorney, Agent, or Firm*—Goodwin Procter LLP

(57) ABSTRACT

The invention relates to novel pyridine derivatives of formula 1, to their preparation and to their use as medicaments, in particular for treating tumors

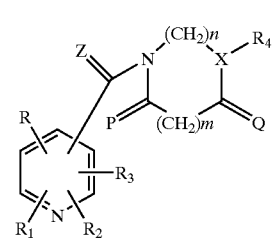

(1)

48 Claims, No Drawings

HETEROARY1 DERIVATIVES AND THEIR USE AS MEDICAMENTS

FIELD OF THE INVENTION

The invention relates to novel heteroaryl derivatives to their preparation and to their use as medicaments, in particular for treating tumors.

DESCRIPTION OF INVENTION

According to one aspect of the present invention, novel pyridine derivatives are provided of formula 1

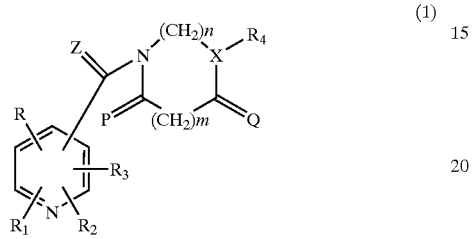

wherein

R, $R_1$, $R_2$, $R_3$ can be attached to any of the pyridine carbon atoms $C_{2-6}$, and are the same or different and independently of one another are hydrogen, hydroxyl straight-chain or branched $C_{1-8}$ alkyl, $C_{3-7}$ cycloalkyl, straight-chain or branched $C_{1-8}$ alkylcarbonyl, suitably acetyl, straight-chain or branched $C_{1-8}$ alkoxy, halogen, aryl-$C_{1-8}$ alkoxy, suitably benzyloxy or phenylethyloxy, nitro, amino, mono-$C_{1-4}$ alkylamino, di-$C_{1-4}$ alkylamino, $C_{1-8}$ alkoxycarbonylamino, $C_{1-6}$ alkoxycarbonylamino-$C_{1-8}$ alkyl, cyano, straight-chain or branched cyano-$C_{1-6}$ alkyl, carboxyl, $C_{1-8}$ alkoxycarbonyl, $C_{1-4}$ alkyl which is substituted by one or more fluorine atoms, suitably the trifluoromethyl group, carboxy-$C_{1-8}$ alkyl or $C_{1-8}$ alkoxycarbonyl-$C_{1-6}$ alkyl $C_{2-6}$ alkenyl, suitably allyl, $C_{2-6}$ alkynyl, suitably ethynyl or propargyl, straight-chain or branched cyano-$C_{1-6}$ alkyl, suitably cyanomethyl, aryl, where the aryl radical may be unsubstituted or mono- or polysubstituted by the same or different substituents from the group of halogen, straight-chain or branched $C_{1-8}$ alkyl, $C_{3-7}$ cycloalkyl, carboxyl, straight-chain or branched $C_{1-8}$ alkoxycarbonyl, suitably tert-butoxycarbonyl, by trifluoromethyl, hydroxyl, straight-chain or branched $C_{1-8}$ alkoxy, suitably methoxy or ethoxy, benzyloxy, nitro, amino, mono-$C_{1-4}$ alkylamino, di-$C_{1-4}$ alkylamino, cyano, straight-chain or branched cyano-$C_{1-6}$ alkyl, where additionally R and $R_1$ and/or $R_2$ and $R_3$ may form a fused aromatic 6-membered ring with the pyridine ring forming a quinoline or acridine ring which can be substituted at any C atom ring position by the radicals R, $R_1$, $R_2$ and $R_3$ having the meanings mentioned above;

Z is oxygen or sulfur, where the radical

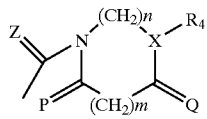

substituted on the pyridine heterocycle can be attached to C atoms $C_2$–$C_6$ of the pyridine ring;

P, Q are independently of one another oxygen or in each case two hydrogen atoms as in —$CH_2$—;

X is nitrogen or C-$R_5$, where $R_5$ is hydrogen or $C_{1-6}$ alkyl;

n,m are independently of one another a cardinal number between 0 and 3, with the proviso that in the case when n is 0, X is a $CR_5R_6$ group where $R_5$ and $R_6$ are independently of one another hydrogen or $C_{1-6}$ alkyl and that the nitrogen atom adjacent to the C=Z group is substituted by a hydrogen atom or a $C_{1-6}$ alkyl group;

$R_4$ a straight-chain or branched $C_{1-20}$ alkyl radical which can be saturated or unsaturated, with one to three double and/or triple bonds, and which can be unsubstituted or can be substituted at the same or different C atoms by one, two or more aryl, heteroaryl, halogen, $C_{1-6}$ alkoxy, amino, mono-$C_{1-4}$ alkylamino, cyano, —C=NH (NH$_2$), or di-$C_{1-4}$ alkylamino; a $C_{6-14}$ aryl radical, carboxy, $C_{1-4}$ alkoxycarbonyl, $C_{6-14}$ aryl-$C_{1-4}$ alkyl radical or a $C_{2-10}$ heteroaryl or $C_{2-10}$ heteroaryl-$C_{1-4}$ alkyl radical which contains one or more heteroatoms of N, O or S, where the $C_{1-4}$ alkyl radical can be unsubstituted or mono- or polysubstituted by the same or different substituents from the group of $C_{1-6}$ alkyl, halogen or oxo (=O),, and where the $C_{6-14}$ aryl or $C_{2-10}$ heteroaryl radical can be unsubstituted or mono- or polysubstituted by the same or different substituents from the group of straight-chain or branched $C_{1-8}$ alkyl, $C_{3-7}$ cycloalkyl, halogen, cyano, $C_{1-6}$ alkoxycarbonylamino, $C_{1-4}$ alkoxy, carboxyl, $C_{1-8}$ alkoxycarbonyl, straight-chain or branched $C_{1-4}$ alkyl which is substituted by one or more fluorine atoms, suitably trifluoromethyl, hydroxyl, straight-chain or branched $C_{1-8}$ alkoxy, suitably methoxy or ethoxy, where adjacent oxygen atoms can also be linked by $C_{1-2}$ alkylene groups, suitably by a methylene group, benzyloxy, nitro, amino, mono-$C_{1-4}$ alkylamino, di-$C_{1-4}$ alkylamino, aryl, which for its part can be unsubstituted or mono- or polysubstituted by the same or different substituents from the group of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, suitably methoxy or ethoxy, benzyloxy, nitro, amino, mono-$C_{1-4}$ alkylamino, di-$C_{1-4}$ alkylamino, cyano, straight-chain or branched cyano-$C_{1-6}$ alkyl;

and their structural isomers and stereoisomers, particularly tautomers, diastereomers and enantiomers, and their pharmaceutically acceptable salts, particularly acid addition salts, are provided.

Thus, for example, the compounds of formula (1) according to the present invention which have one or more centers of chirality and which are present as racemates can be separated by methods known per se into their optical isomers, i.e. enantiomers or diastereomers. The separation can be carried out by column separation on chiral phases or by recrystallization from an optically active solvent or using an optically active acid or base or by derivatization with an optically active reagent, such as, for example, an optically active alcohol, and subsequent removal of the radical.

Furthermore, the pyridine derivatives of formula (1) of the present invention can be converted into their salts with inorganic or organic acids, in particular, for pharmaceutical use, into their pharmaceutically acceptable salts. Acids which are suitable for this purpose include hydrochloric acid, hydrobromic acid, sulfuric acid, phosphoric acid, fumaric acid, succinic acid, lactic acid, citric acid, acetic acid, tartaric acid, malic acid, embonic acid, malonic acid, trifluoroacetic acid or maleic acid.

Moreover, the compounds of formula (1) of the present invention can, if they contain a sufficiently acidic group, such as a carboxyl group, be converted into their salts with inorganic or organic bases, particularly for pharmaceutical use, into their pharmaceutically acceptable salts. Bases which are suitable for this purpose include sodium hydroxide, potassium hydroxide, calcium hydroxide, lysine, cyclohexylamine, ethanolamine, diethanolamine and triethanolamine.

According to a suitable embodiment, pyridine derivatives of formula 1 are provided in which R, R1, R2, R3, X, Z, P, Q, n and m have the meanings given above Y is a substituent group of the same or different substituents of $C_{1-6}$ alkyl, halogen, nitro, amino, mono-$C_{1-6}$ alkylamino, di-$C_{1-6}$ alkylamino, hydroxyl, $C_{1-6}$ alkoxy, benzyloxy, carboxyl, $C_{1-6}$ alkoxycarbonyl, $C_{1-6}$ alkoxycarbonylamino, $C_{1-6}$ alkyl mono- or polysubstituted with fluorine, suitably trifluoromethyl, $C_{6-10}$ aryl, and $C_{6-10}$ aryl-$C_{1-6}$ alkyl, and $R_4$ is a straight-chain or branched $C_{1-20}$ alkyl radical which can be saturated or unsaturated, with one to three double and/or triple bonds, and which can be unsubstituted or substituted on the same or different C atoms by one, two or more aryl, heteroaryl, halogen, $C_{1-6}$ alkoxy, amino, mono-$C_{1-4}$ alkylamino or di-$C_{1-4}$ alkylamino;

a phenyl ring or a naphthyl ring, each of which can be unsubstituted or mono- or polysubstituted by the same or different substituents from the group of straight-chain or branched $C_{1-8}$ alkyl, $C_{3-7}$ cycloalkyl, halogen, cyano, $C_{1-6}$ alkoxycarbonylamino, $C_{1-6}$ alkoxy, carboxyl, $C_{1-8}$ alkoxycarbonyl, straight-chain or branched $C_{1-6}$ alkyl which is substituted by one or more fluorine atoms, suitably trifluoromethyl, hydroxyl, straight-chain or branched $C_{1-8}$ alkoxy, suitably methoxy or ethoxy, where adjacent oxygen atoms can also be linked by $C_{1-2}$ alkylene groups, suitably a methylene group, benzyloxy, nitro, amino, mono-$C_{1-4}$ alkylamino, di-$C_{1-4}$ alkylamino, aryl, which can be unsubstituted or mono- or polysubstituted by the same or different substituents from the group of straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, suitably methoxy or ethoxy, benzyloxy, nitro, amino, mono-$C_{1-4}$ alkylamino, di-$C_{1-4}$ alkylamino, cyano, straight-chain or branched cyano-$C_{1-6}$ alkyl;

a 2-, 4-, 5- or 6-pyrimidinyl radical, or a 2-, 4-, 5- or 6-pyrimidinyl -$C_{1-4}$ alkyl radical, wherein the $C_{1-4}$ alkyl radical can be unsubstituted or mono- or polysubstituted by identdal or different substituents from the group of $C_{1-6}$ alkyl, halogen or oxo (=O),, and the 2-, 4-, 5- or 6-pyrimidinyl radical can be unsubstituted or mono- to trisubstituted by the same or different substituents from the group of hydrogen, or Y;

a 3-, 4-, 5- or 6-pyridazinyl radical, or a 3-, 4-, 5- or 6-pyridazinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O),, and the 3-, 4-, 5- or 6-pyridazinyl radical can be unsubstituted or mono- or up to trisubstituted by the same or different substituents from the group of hydrogen, or Y;

a 2-, 3-, 5- or 6-pyrazinyl radical, or a 2-, 3-, 5- or 6-pyrazinyl-$C_{1-4}$ alkyl radical, wherein the $C_{1-4}$ alkyl radical can be unsubstituted or mono- or polysubstituted by identdal or different substituents from the group of $C_{1-6}$ alkyl, halogen or oxo (=O),, and the 2-, 3-, 5- or 6-pyrazinyl radical can be unsubstituted or mono- to trisubstituted by the same or different substituents from the group of hydrogen, or Y;

a 3-, 4-, 5-, 6-, 7-, or 8-cinnolinyl radical, or a 3-, 4-, 5-, 6-, 7-, or 8-cinnolinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O),, and the 3-, 4-, 5-, 6-, 7-, or 8-cinnolinyl radical can be unsubstituted or mono- or up to pentasubstituted by the same or different substituents from the group of hydrogen, or Y;

a 2-, 4-, 5-, 6-, 7-, or 8-quinazolinyl radical, or a 2-, 4-, 5-, 6-, 7-, or 8-quinazolinyl-$C_{1-4}$ alkyl radical, wherein the $C_{1-4}$ alkyl radical can be unsubstituted or mono- or polysubstituted by the same or different substituents from the group of hydrogen, $C_{1-6}$ alkyl, halogen or oxo (=O),, and the 2-, 4-, 5-, 6-, 7-, or 8-quinazolinyl radical can be unsubstituted or mono- or up to pentasubstituted by the same or different substituents from the group of hydrogen, or Y;

a 2-, 3-, 5-, 6-, 7-, or 8-quinoxalinyl radical, or a 2-, 3-, 5-, 6-, 7-, or 8-quinoxalinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O),, and the 2-, 3-, 5-, 6-, 7-, or 8-quinoxalinyl radical can be unsubstituted or mono- or up to pentasubstituted by the same or different substituents from the group of hydrogen, or Y;

a 1-, 4-, 5-, 6-, 7-, or 8-phthalazinyl radical, or a 1-, 4-, 5-, 6-, 7-, or 8-phthalazinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O),, and the 1-, 4-, 5-, 6-, 7-, or 8-phthalazinyl radical can be unsubstituted or mono- to pentasubstituted by the same or different substituents from the group of hydrogen, or Y;

a 2-, 3-, 4-, 5-, 6-, 7- or 8-quinolyl radical, or a 2-, 3-, 4-, 5-, 6-, 7 or 8-quinolyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O),, and the 2-, 3-, 4-, 5-, 6-, 7- or 8-quinolyl radical can be unsubstituted or mono- or up to hexasubstituted by the same or different substituents from the group of hydrogen, or Y;

a 1-, 3-, 4-, 5-, 6-, 7- or 8-isoquinolyl radical, or a 1-, 3-, 4-, 5-, 6-, 7-or 8-isoquinolyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O),, and the 1-, 3-, 4-, 5-, 6-, 7- or 8-isoquinolyl radical can be unsubstituted or mono- or up to hexasubstituted by the same or different substituents from the group of hydrogen, or Y;

a 2-, 6-, 8- or 9-[9H]-purinyl radical, or a 2-, 6-, 8- or 9-[9H]-purinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O),, and the 2-, 6-, 8- or 9-[9H]-purinyl radical can be unsubstituted or mono- to trisubstituted by the same or different substituents from the group of hydrogen, or Y;

a 2-, 6-, 7- or 8-[7H]-purinyl radical, or a 2-, 6-, 7- or 8-[7H]-purinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O),, and the 2-, 6-, 7- or 8-[7H]-purinyl radical can be unsubstituted or mono- or up to trisubstituted by the same or different substituents from the group of hydrogen, or Y;

a 1-, 2-, 3-, 4-, 5-, 6-, 7-, 8- or 9-acridinyl radical, or a 1-, 2-, 3-, 4-, 5-, 6-, 7-, 8-or 9-acridinyl-$C_{1-4}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 1-, 2-, 3-, 4-, 5-, 6-, 7-, 8- or 9-acridinyl radical can be unsubstituted or mono- or up to octasubstituted by the same or different substituents from the group of hydrogen, or Y;

a 1-, 2-, 3-, 4-, 5-, 6-, 7-, 8- or 9-phenanthridinyl radical, or a 1-, 2-, 3-, 4-, 5-, 6-, 7-, 8- or 9-phenanthridinyl-$C_{1-6}$ alkyl radical, wherein the $C_{1-6}$ alkyl radical can be unsubstituted or mono- or polysubstituted by the same or different substituents from the group of hydrogen, $C_{1-6}$ alkyl, halogen or oxo (=O),, and the 1-, 2-, 3-, 4-, 5-, 6-, 7-, 8- or 9-phenanthridinyl radical can be unsubstituted or mono- or up to octasubstituted by Y;

a 2-, 3-, 4-, 5- or 6-pyridyl radical, which can be unsubstituted or mono- or up to tetrasubstituted by Y;

a 2-, 3-, 4-, 5- or 6-pyridinyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 2-, 3-, 4-, 5- or 6-pyridinyl radical can be unsubstituted or mono- or up to tetrasubstituted by the same or different substituents from the group of hydrogen, or Y;

a 2-, 3-, 4- or 5-thienyl radical, or a 2-, 3-, 4- or 5-thienyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 2-, 3-, 4- or 5-thienyl radical can be unsubstituted or mono- to trisubstituted by the same or different substituents from the group of hydrogen, or Y;

a 2-, 4-, or 5-thiazolyl radical, or a 2-, 4-, or 5-thiazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 2-, 4-, or 5-thiazolyl radical can be unsubstituted or mono- or disubstituted by the same or different substituents from the group of hydrogen, or Y;

a 3-, 4-, or 5-isothiazolyl radical, or a 3-, 4-, or 5-isothiazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 3-, 4-, or 5-isothiazolyl radical can be unsubstituted or mono- or disubstituted by the same or different substituents from the group of hydrogen, or Y;

a 2-, 4-, 5-, 6-, or 7-benzothiazolyl radical, or a 2-, 4-, 5-, 6-, or 7-benzothiazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 2-, 4-, 5-, 6-, or 7-benzothiazolyl radical can be unsubstituted or mono- to tetrasubstituted by the same or different substituents from the group of hydrogen, or Y;

a 1-, 2-, 4-, or 5-imidazolyl radical, or a 1-, 2-, 4-, or 5-imidazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 1-, 2-, 4-, or 5-imidazolyl radical can be unsubstituted or mono- or up to trisubstituted by the same or different substituents from the group of hydrogen, or Y;

a 1-, 3-, 4-, or 5-pyrazolyl radical, or a 1-, 3-, 4- or 5-pyrazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 1-, 3-, 4- or 5-pyrazolyl radical can be unsubstituted or mono- or up to trisubstituted by the same or different substituents from the group of hydrogen, or Y;

a 1-, 2-, 3-, 4-, or 5-pyrrolyl radical, or a 1-, 2-, 3-, 4-, or 5-pyrrolyl-$C_{1-6}$ -alkyl radical, wherein the $C_{1-6}$ alkyl radical can be unsubstituted or mono- or polysubstituted by the same or different substituents from the group of $C_{1-6}$ alkyl, halogen or oxo (=O),, and the 1-, 2-, 3-, 4- or 5-pyrrolyl radical can be unsubstituted or mono- to tetrasubstituted by the same or different substituents from the group of hydrogen, or Y;

a 1-, 3-, or 5-[1.2.4]-triazolyl radical, or a 1-, 3-, or 5-[1.2.4]-triazolyl -$C_{1-6}$ alkyl radical, wherein the $C_{1-6}$ alkyl radical can be unsubstituted or mono- or polysubstituted by the same or different substituents from the group of hydrogen, $C_{1-6}$ alkyl, halogen or oxo (=O),, and the 1-, 3-, or 5-[1.2.4]-triazolyl radical can be unsubstituted or mono- or disubstituted by Y;

a 1-, 4-, or 5-[1.2.3]-triazolyl radical, or a 1-, 4-, or 5-[1.2.3]-triazolyl -$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 1-, 4-, or 5-[1.2.3]-triazolyl radical can be unsubstituted or mono- or disubstituted by the same or different substituents from the group of hydrogen, or Y;

a 1- or 5-[1H]-tetrazolyl radical, or a 1-, or 5-[1H]-tetrazolyl-$(C_1-C_6)$-alkyl radical, wherein the $C_{1-6}$ alkyl radical can be unsubstituted or mono- or polysubstituted by the same or different substituents from the group of $C_{1-6}$ alkyl, halogen or oxo (=O),, and the 1-, or 5-[1H]-tetrazolyl radical can be unsubstituted or substituted by hydrogen, or Y;

a 2- or 5-[2H]-tetrazoyl radical, or a 2- or 5-[2H]-tetrazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 2- or 5-[2H]-tetrazolyl radical can be unsubstituted or substituted by hydrogen, or Y;

a 2-, 4-, or 6-[1.3.5]-triazinyl radical, or a 2-, 4-, or 6-[1.3.5]-triazinyl -$C_{1-6}$ alkyl radical, wherein the $C_{1-6}$ alkyl radical can be unsubstituted or mono- or polysubstituted by the same or different substituents from the group of hydrogen, or Y;

a 2-, 4-, or 5-oxazolyl radical, or a 2-, 4-, or 5-oxazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 2-, 4-, or 5-oxazolyl radical can be unsubstituted or mono- or disubstituted by the same or different substituents from the group of hydrogen, or Y;

a 3-, 4-, or 5-isoxazolyl radical, or a 3-, 4-, or 5-isoxazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 3-, 4-, or 5-isoxazolyl radical can be unsubstituted or mono- or disubstituted by the same or different substituents from the group of hydrogen, or Y;

a 1-, 2-, 3-, 4-, 5-, 6- or 7-indolyl radical, or a 1-, 2-, 3-, 4-, 5-, 6-, or 7-indolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O),, and the 1-, 2-, 3-, 4-, 5-, 6- or 7-indolyl radical can be unsubstituted or mono- to hexasubstituted by the same or different substituents from the group of hydrogen, or Y, and the isomers, in particular tautomers, diastereomers and enantiomers, and the pharmaceutically acceptable salts, particularly acid addition salts thereof.

According to a further embodiment of the present invention, pyridine derivatives of formula (1) are provided in which R, $R_1$, $R_2$, $R_3$, X, Z, P, Q, n and m have the meanings given above and $R_4$ is phenyl which is unsubstituted or substituted by one to five the same or different $C_{1-6}$ alkoxy groups, wherein adjacent oxygen atoms can also be linked by $C_{1-2}$ alkylene groups.

According to a further embodiment of the present invention, pyridine derivatives of formula (1) are provided in which $R_4$ has the meanings given above, R, $R_1$, $R_2$, $R_3$ are each a hydrogen atom, Z is an oxygen atom, X is a nitrogen atom, P and Q each represent two hydrogen atoms as in —CH2—, m is zero and n is 2.

According to a further embodiment of the present invention, pyridine derivatives of formula (1) are provided in which R, $R_1$, $R_2$, $R_3$, X, Z, P, Q, n and m have the meanings given above, and $R_4$ is 3,5-dimethoxyphenyl.

According to yet a further embodiment of the present invention, pyridine derivatives of formula (1) are provided in which R, $R_1$, $R_2$, $R_3$ are each a hydrogen atom, Z is an oxygen atom, X is a nitrogen atom, P and Q are each two hydrogen atoms as in —CH2—, m is zero, n is 2, and $R_4$ is a 3,5-dimethoxyphenyl radical.

According to a further aspect of the present invention, a process is provided for preparing pyridine derivatives of formula (1), by reacting a pyridine carboxylic acid of formula (2)

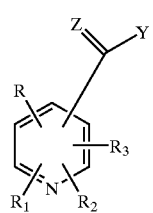

(2)

in which R, R1, R2, R3 have the meanings given above, Z is an oxygen or sulfur atom, and Y represents a leaving group such as halogen, hydroxyl, (C1–C6)-alkoxy, such as methoxy or ethoxy, —O-tosyl, —O-mesyl or imidazolyl, with an amine of formula (3)

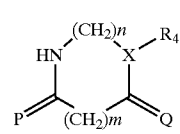

(3)

in which R4, X, P, Q, m and n are as defined above, and optionally using diluents and auxiliaries.

Synthesis Route

The compounds of formula 1 can be obtained according to the following reaction scheme 1:

Scheme 1

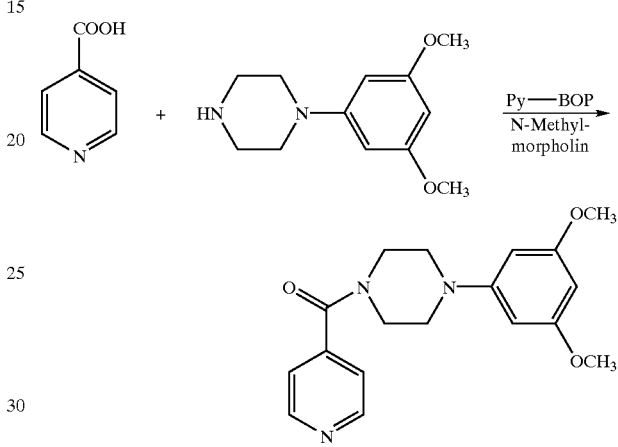

The starting materials of formulae (2) and (3) are either commercially available or can be prepared by procedures known per se. The starting materials of formulae (2) and (3) are useful intermediates for preparing the pyridine derivatives of formula (1) of the present invention.

The solvents and auxiliaries to be optionally used, and the reaction parameters to be used, such as reaction temperature and reaction time, are known from the literature or are familiar to the person skilled in the art owing to his expert knowledge.

The pyridine derivatives of formula (1) of the present invention are suitable as medicaments, particularly as anti-tumor agents, for treating mammals, particularly man, and also domestic animals such as horses, cattle, dogs, cats, rabbits, sheep, poultry and the like.

According to a further aspect of the invention, a therapeutic method is provided for controlling tumors in mammals, particularly man, by administering at least one pyridine derivative of formula (1) to a mammal in an amount effective for the treatment of the tumor. The therapeutically effective dose of the pyridine derivative according to the invention which is to be administered for the treatment depends inter alia on the nature and the stage of the oncosis, the age and the sex of the patient, the type of administration and the duration of the treatment and can be determined by routine dosage ranging. Administration can take place orally, rectally, buccally (for example sublingually), parenterally (for example subcutaneously, intramuscularly, intradermally or intravenously), topically or transdermally.

According to a further aspect of the prinvention, medicaments are provided for the treatment of tumors, comprising as active ingredient, at least one pyridine derivative of formulae (1) or a pharmaceutically acceptable salt thereof, optionally together with conventional pharmaceutically acceptable auxiliaries, additives and carriers. These can be solid, semisolid, liquid or aerosol preparations. Suitable solid preparations are, for example, capsules, powders, granules, tablets. Suitable semisolid preparations are, for example, ointments, creams, gels, pastes, suspensions, oil-in-water and water-in-oil emulsions. Suitable liquid preparations are, for example, sterile aqueous preparations for parenteral administration which are isotonic with the blood of the patient.

The invention is illustrated in more detail by the following example, without being restricted to the example.

1-(3,5-Dimethoxyphenyl)-4-(4-pyridyl-carbonyl) piperazine 5 g (45.8 mmol) of pyridine-4-carboxylic acid were suspended with stirring in 150 ml of DMF. With further stirring, 6.93 g (68.5 mmol) of N-methylmorpholine and then a solution of 35.6 g (68.5 mmol) of Py-BOP (1-benzotriazolyltripyrrolidinophosphonium hexafluorophosphate) and 10.18 g (45.8 mmol) of 1-(3,5-dimethoxyphenyl)piperazine in 60 ml of DMF were added to this mixture. The mixture was stirred at room temperature for 24 hours, the DMF was distilled off under reduced pressure and the residue was purified on a silica gel column (Kieselgel 60, from Merck AG, Darmstadt) using the mobile phase dichloromethane/methanol/25 percent ammonia (90:10:1 v/v/v).

Yield: 12.34 g (82.3% of theory)

m.p.: 94–96° C.

TABLE 1

New Pyridine-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 1 | 2-Cl | H | H | 6-Cl | N | O | 2 | 0 | $H_2$ | $H_2$ | | 21418 | 355 |
| 2 | 2-Cl | H | H | 6-Cl | N | O | 2 | 0 | $H_2$ | $H_2$ | | 21432 | 397 |
| 3 | 2-Cl | H | H | 6-Cl | N | O | 2 | 0 | $H_2$ | $H_2$ | | 21464 | 405 |
| 4 | 2-Cl | H | H | 6-Cl | N | O | 2 | 0 | $H_2$ | $H_2$ | | 21468 HCl-Salz | 339 |
| 5 | 2-Cl | H | H | 6-Cl | N | O | 2 | 0 | $H_2$ | $H_2$ | | 21466 HCl-Salz | 427 |

TABLE 2

New Pyridine-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 6 | 2-Cl | H | H | 6-Cl | N | O | 2 | 0 | $H_2$ | $H_2$ | | 21419 | 367 |
| 7 | 2-Cl | H | H | 6-Cl | N | O | 2 | 0 | $H_2$ | $H_2$ | | 21433 | 397 |
| 8 | 2-Cl | H | H | 6-Cl | N | O | 2 | 0 | $H_2$ | $H_2$ | | 21465 HCl-Salz | 339 |
| 9 | 2-Cl | H | H | 6-Cl | N | O | 2 | 0 | $H_2$ | $H_2$ | | 21463 | 463 |
| 10 | 2-Cl | H | H | 6-Cl | N | O | 2 | 0 | $H_2$ | $H_2$ | | 21723 | 505 |

TABLE 3

New Pyridine-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 11 | 2-Cl | H | H | 6-Cl | N | O | 2 | 0 | $H_2$ | $H_2$ | | 22916 | 337 |
| 12 | 2-Cl | H | H | 6-Cl | N | O | 2 | 0 | $H_2$ | $H_2$ | | 22914 | 427 |
| 13 | H | H | H | H | N | O | 2 | 0 | $H_2$ | $H_2$ | | 22919 | 328 |
| 14 | 2-Cl | H | H | 6-Cl | N | O | 2 | 0 | $H_2$ | $H_2$ | | 23001 | 382 |
| 15 | 2-Cl | H | H | 6-Cl | N | O | 2 | 0 | $H_2$ | $H_2$ | | 23055 | 435 |

TABLE 4

New Pyridine-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 16 | 2-Cl | H | H | 6-Cl | N | O | 2 | 0 | $H_2$ | $H_2$ | | 22915 | 367 |
| 17 | H | H | H | H | N | O | 2 | 0 | $H_2$ | $H_2$ | | 22920 | 358 |
| 18 | 2-Cl | H | H | 6-Cl | N | O | 2 | 0 | $H_2$ | $H_2$ | | 22918 | 353 |

TABLE 4-continued

New Pyridine-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 19 | 2-Cl | H | H | 6-Cl | N | O | 2 | 0 | $H_2$ | $H_2$ | | 23195 | 352 |
| 20 | 2-Cl | H | H | 6-Cl | N | O | 2 | 0 | $H_2$ | $H_2$ | | 22917 | 333 |

TABLE 5

New Pyridine-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 21 | 2-Cl | H | H | 6-Cl | N | O | 2 | 0 | $H_2$ | $H_2$ | | 24085 | 362 |
| 22 | 2-Cl | H | H | 6-Cl | N | O | 2 | 0 | $H_2$ | $H_2$ | | 24087 | 338 |
| 23 | 2-Cl | H | H | 6-Cl | N | O | 2 | 0 | $H_2$ | $H_2$ | | 24086 | 338 |
| 24 | 2-Cl | H | H | 6-Cl | N | O | 2 | 0 | $H_2$ | $H_2$ | | 24152 | 415 |
| 25 | 2-Cl | H | H | 6-Cl | N | O | 2 | 0 | $H_2$ | $H_2$ | | 24202 | 377 |

TABLE 6

New Pyridine-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 26 | H | H | H | H | N | O | 2 | 0 | $H_2$ | $H_2$ | | 32848 | 269 |
| 27 | H | H | H | H | N | O | 2 | 0 | $H_2$ | $H_2$ | | 35655 | 278 |
| 28 | H | H | H | H | N | O | 2 | 0 | $H_2$ | $H_2$ | | 36134 | 358 |
| 29 | H | H | H | H | N | O | 2 | 0 | $H_2$ | $H_2$ | | 36138 | 268 |
| 30 | H | H | H | H | N | O | 2 | 0 | $H_2$ | $H_2$ | | 32902 | 270 |

TABLE 7

New Pyridine-Derivatives with antitumoral activity

| Ex. | R | $R_1$ | $R_2$ | $R_3$ | X | Z | n | m | P | Q | $R_4$ | Code-Nr. | m/e (M + H) |
|---|---|---|---|---|---|---|---|---|---|---|---|---|---|
| 31 | H | H | H | H | N | O | 2 | 0 | $H_2$ | $H_2$ | | 35656 | 296 |
| 32 | H | H | H | H | N | O | 2 | 0 | $H_2$ | $H_2$ | | 41410 | 310 |
| 33 | H | H | H | H | N | O | 2 | 0 | $H_2$ | $H_2$ | | 41437 | 365 |
| 34 | H | H | H | H | N | O | 2 | 0 | $H_2$ | $H_2$ | | 41455 | 326 |
| 35 | 2-$OCH_3$ | H | H | 6-$OCH_3$ | N | O | 2 | 0 | $H_2$ | $H_2$ | | 24204 | 388 |

We claim:

1. A compound of formula 1

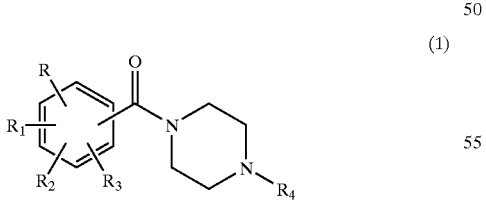

(1)

wherein

R, $R_1$, $R_2$, $R_3$ can be attached to any of the pyridine carbon atoms $C_2$ to $C_8$, and can be the same or different and independently of one another are hydrogen, hydroxyl, straight-chain or branched $C_{1-8}$ alkyl, $C_{3-7}$ cycloalkyl, straight-chain or branched $C_{1-8}$ alkylcarbonyl, straight-chain or branched $C_{1-8}$ alkoxy, halogen, aryl-$C_{1-8}$ alkoxy, nitro, amino, mono-$C_{1-4}$ alkylamino, di-$C_{1-4}$ alkylamino, $C_{1-8}$ alkoxycarbonylamino, $C_{1-6}$ alkoxycarbonylamino-$C_{1-8}$ alkyl, cyano, straight-chain or branched cyano-$C_{1-6}$ alkyl, carboxyl, $C_{1-8}$ alkoxycarbonyl, $C_{1-4}$ alkyl which is substituted by one or more fluorine atoms, carboxy-$C_{1-8}$ alkyl or $C_{1-8}$ alkoxycarbonyl-$C_{1-6}$ alkyl, $C_{2-6}$ alkenyl, $C_{2-6}$ alkynyl, straight-chain or branched cyano-$C_{1-6}$ alkyl, aryl, where the aryl radical can be unsubstituted or mono- or polysubstituted by the same or different substituents from the group consisting of halogen, straight-chain or branched $C_{1-8}$ alkyl, $C_{3-7}$ cycloalkyl, carboxyl, straight-chain or branched $C_{1-8}$ alkoxycarbonyl, trifluoromethyl, hydroxyl, straight-chain or branched $C_{1-8}$ alkoxy, benzyloxy, nitro, amino, mono-$C_{1-4}$ alkylamino, di-$C_{1-4}$ alkylamino, cyano, straight-chain or branched cyano-$C_{1-6}$ alkyl R and $R_1$ and/or $R_2$ and $R_3$ can form a fused aromatic 6-membered ring with the pyridine ring forming a quinoline or acridine ring which can be substituted at any C atom ring position by the radicals R, $R_1$, $R_2$ and $R_3$ having the meanings mentioned above;

R$_4$ is a straight-chain or branched C$_{4-20}$ alkyl radical which can be saturated or unsaturated, with one to three double and/or triple bonds, and which can be unsubstituted or can optionally be substituted at the same or different C atoms by one, two or more aryl, heteroaryl, halogen, C$_{1-6}$ alkoxy, amino, mono-C$_{1-4}$ alkylamino, cyano —C=NH(NH$_2$) or di-C$_{1-4}$ alkylamino; a C$_{6-14}$ aryl radical, carboxy, C$_{1-4}$ alkoxycarbonyl, C$_{6-14}$ aryl-C$_{2-4}$ alkyl radical, or a C$_{2-10}$ heteroaryl, or C$_{2-10}$ heteroaryl-C$_{1-4}$ alkyl radical which contains one or more heteroatoms of N, O or S, where the C$_{1-4}$ alkyl radical can be unsubstituted or mono- or polysubstituted by the same or different substituents from the group consisting of C$_{1-6}$ alkyl, halogen or oxo (=O), and where the C$_{6-14}$ aryl or C$_{2-10}$ heteroaryl radical can be unsubstituted or mono- or polysubstituted by the same or different substituents from the group consisting of straight-chain or branched C$_{1-8}$ alkyl, C$_{3-7}$ cycloalkyl, halogen, cyano, C$_{1-6}$ alkoxycarbonylamino, C$_{1-6}$ alkoxy, carboxyl, C$_{1-8}$ alkoxycarbonyl, straight-chain or branched C$_{1-6}$ alkyl which is substituted by one or more fluorine atoms, hydroxyl, straight-chain or branched C$_{1-8}$ alkoxy, where adjacent oxygen atoms can also be linked by C$_{1-2}$ alkylene groups, benzyloxy, nitro, amino, mono-C$_{1-4}$ alkylamino, di-C$_{1-4}$ alkylamino, aryl, which can be unsubstituted or mono- or polysubstituted by the same or different substituents from the group of straight-chain or branched C$_{1-8}$ alkyl, C$_{3-7}$ cycloalkyl, carboxyl, straight-chain or branched C$_{1-8}$ alkoxycarbonyl, trifluoromethyl, hydroxyl, straight-chain or branched C$_{1-8}$ alkoxy, benzyloxy, nitro, amino, mono-C$_{1-4}$ alkylamino, di-C$_{1-4}$ alkylamino, cyano, straight-chain or branched cyano-C$_{1-6}$ alkyl;

or their structural isomers or stereoisomers, including tautomers, diastereomers or enantiomers, or their pharmaceutically acceptable salts.

2. A compound of formula 1 of claim 1, wherein in R, R$_1$, R$_2$, and R$_3$, said C$_{1-8}$ alkylcarbonyl is acetyl, said C$_{1-8}$ alkoxy is benzyloxy or phenylethoxy, said fluorine atoms are trifluoromethyl, said C$_{2-6}$ alkenyl is allyl, said C$_{2-6}$ alkynyl is ethynyl or propargyl, said cyano-C$_{1-6}$ alkyl is cyanomethyl, said C$_{1-8}$ alkoxy carbonyl is tert-butoxycarbonyl, and said C$_{1-8}$ alkoxy is methoxy or ethoxy, and in R$_4$ said fluorine atoms are trifluoromethyl, said C$_{1-8}$ alkoxy is methoxy or ethoxy, and said C$_{1-2}$ alkylene group is a methylene group.

3. A compound of formula 1 of claim 1, wherein R, R$_1$, R$_2$, and R$_3$ have the meanings given in claim 1

Y is a substituent group of the same or different substituents of C$_{1-6}$ alkyl, halogen, nitro, amino, mono-C$_{1-6}$ alkylamino, di-C$_{1-6}$ alkylamino, hydroxyl, C$_{1-6}$ alkoxy, benyloxy, carboxyl, C$_{1-6}$ alkoxycarbonyl, C$_{1-6}$ alkoxycarbonylamino, C$_{1-6}$ alkyl mono- or polysubstituted with fluorine, C$_{6-10}$ aryl, and C$_{6-10}$ aryl-C$_{1-6}$ alkyl, and R4 is a straight-chain or branched C$_{4-20}$ alkyl radical which can be saturated or unsaturated, with one to three double and/or triple bonds, and which can be unsubstituted or substituted on the same or different C atoms by one, two or more aryl, heteroaryl, halogen, C$_{1-6}$ alkoxy, amino, mono-C$_{1-4}$ alkylamino or di-C$_{1-4}$ alkylamino; a phenyl ring or a naphthyl ring, each of which can be unsubstituted or mono- or polysubstituted by the same or different substituents from the group of straight-chain or branched C$_{2-8}$ alkyl, C$_{3-7}$ cycloalkyl, bromine atom or atoms, iodine atoms or atoms, cyano, C$_{1-6}$ alkoxycarbonylamino, C$_{1-6}$ alkoxy, C$_{1-8}$ alkoxycarbonyl, hydroxyl, straight-chain or branched C$_{1-8}$ alkoxy, benzyloxy, amino, mono-C$_{1-4}$ alkylamino, di-C$_{1-4}$ alkylamino, aryl, which can be unsubstituted or mono- or polysubstituted by the same or different substituents from the group of straight-chain or branched C$_{1-8}$ alkoxycarbonyl, trifluoromethyl, hydroxyl, straight-chain or branched C$_{1-8}$ alkoxy, benzyloxy, nitro, amino, mono-C$_{1-4}$ alkylamino, di-C$_{1-4}$ alkylamino, cyano, straight-chain or branched cyano-C$_{1-6}$ alkyl;

a 2-, 4-, 5- or 6-pyrimidinyl radical, or a 2-, 4-, 5- or 6-pyrimidinyl-C$_{1-4}$ alkyl radical, wherein the C$_{1-4}$ alkyl radical can be unsubstituted or mono- or polysubstituted by the same or different substituents from the group consisting of C$_{1-6}$ alkyl, halogen and oxo (=O), and the 2-, 4-, 5- or 6-pyrimidinyl radical can be unsubstituted or mono- or up to trisubstituted by the same or different substituents from the group of hydrogen or Y;

a 3-, 4-, 5- or 6-pyridazinyl radical, or a 3-, 4-, 5- or 6-pyridazinyl-C$_{1-4}$ alkyl radical, wherein the C$_{1-4}$ alkyl radical can be unsubstituted or mono- or polysubstituted by the same or different substituents from the group of C$_{1-6}$ alkyl, halogen or oxo (=O), and the 3-, 4-, 5- or 6-pyridazinyl radical can be unsubstituted or mono- to trisubstituted by the same or different substituents from the group of hydrogen, or Y;

a 2-, 3-, 5- or 6-pyrazinyl radical, or a 2-, 3-, 5- or 6-pyrazinyl-C$_{1-4}$ alkyl radical, wherein the C$_{1-4}$ alkyl radical can be unsubstituted or mono- or polysubstituted by the same or different substituents from the group of C$_{1-6}$ alkyl, halogen or oxo (=O), and the 2-, 3-, 5- or 6-pyrazinyl radical can be unsubstituted or mono- to trisubstituted by the same or different substituents from the group of hydrogen, or Y;

a 3-, 4-, 5-, 6-, 7-, or 8-cinnolinyl radical, or a 3-, 4-, 5-, 6-, 7-, or 8-cinnolinyl-C$_{1-4}$ alkyl radical, wherein the C$_{1-4}$ alkyl radical can be unsubstituted or mono- or polysubstituted by the same or different substituents from the group of C$_{1-6}$ alkyl, halogen or oxo (=O), and the 3-, 4-, 5-, 6-, 7-, or 8-cinnolinyl radical can be unsubstituted or mono- or up to pentasubstituted by the same or different substituents from the group of hydrogen, or Y;

a 2-, 4-, 5-, 6-, 7-, or 8-quinazolinyl radical, or a 2-, 4-, 5-, 6-, 7-, or 8-quinazolinyl-C$_{1-4}$ alkyl radical, wherein the C$_{1-4}$ alkyl radical can be unsubstituted or mono- or polysubstituted by the same or different substituents from the group of hydrogen, C$_{1-6}$ alkyl, halogen or oxo (=O), and the 2-, 4-, 5-, 6-, 7-, or 8-quinazolinyl radical can be unsubstituted or mono- or up to pentasubstituted by the same or different substituents from the group of hydrogen, or Y;

a 2-, 3-, 5-, 6-, 7-, or 8-quinoxalinyl radical, or a 2-, 3-, 5-, 6-, 7-, or 8-quinoxalinyl-C$_{1-4}$ alkyl radical, where the C$_{1-4}$ alkyl radical can be unsubstituted or mono- or polysubstituted by the same or different substituents from the group of C$_{1-6}$ alkyl, halogen or oxo (=O), and the 2-, 3-, 5-, 6-, 7-, or 8-quinoxalinyl radical can be unsubstituted or mono- to pentasubstituted by the same or different substituents from the group of hydrogen, or Y;

a 1-, 4-, 5-, 6-, 7-, or 8-phthalazinyl radical, or a 1-, 4-, 5-, 6-, 7-, or 8-phthalazinyl-C$_{1-4}$ alkyl radical, where the C$_{1-4}$ alkyl radical can be unsubstituted or mono- or polysubstituted by the same or different substituents from the group consisting of $C_{1-6}$ alkyl, halogen or oxo (=O), and the 1-, 4-, 5-, 6-, 7-, or 8-phthalazinyl radical can be unsubstituted or mono- or up to pentasubstituted by the same or different substituents from the group of hydrogen, or Y;

a 2-, 3-, 4-, 5-, 6-, 7- or 8-quinolyl radical, or a 2-, 3-, 4-, 5-, 6-, 7 or 8-quinolyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 2-, 3-, 4-, 5-, 6-, 7- or 8-quinolyl radical can be unsubstituted or mono- or up to hexasubstituted by the same or different substituents from the group of hydrogen, or Y;

a 1-, 3-, 4-, 5-, 6-, 7- or 8-isoquinolyl radical, or a 1-, 3-, 4-, 5-, 6-, 7- or 8-isoquinolyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 1-, 3-, 4-, 5-, 6-, 7- or 8-isoquinolyl radical can be unsubstituted or mono- or up to hexasubstituted by the same or different substituents from the group of hydrogen, or Y;

a 2-, 6-, 8- or 9-[9H]-purinyl radical, or a 2-, 6-, 8- or 9-[9H]-purinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 2-, 6-, 8- or 9-[9B]-purinyl radical can be unsubstituted or mono- or up to trisubstituted by the same or different substituents from the group of hydrogen, or Y;

a 2-, 6-, 7- or 8-[7H]-purinyl radical, or a 2-, 6-, 7- or 8-[7H]-purinyl-$C_{1-4}$ alkyl radical, wherein the $C_{1-4}$ alkyl radical can be unsubstituted or mono- or polysubstituted by the same or different substituents from the group of $C_{1-6}$ alkyl, halogen or oxo (=O), and the 2-, 6-, 7- or 8-[7H]-purinyl radical can be unsubstituted or mono- or up to trisubstituted by the or different substituents from the group of hydrogen, or Y;

a 1-, 2-, 3-, 4-, 5-, 6-, 7-, 8- or 9-acridinyl radical, or a 1-, 2-, 3-, 4-, 5-, 6-, 7-, 8- or 9-acridinyl-$C_{1-4}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 2-, 3-, 4-, 5-, 6-, 7-, 8- or 9-acridinyl radical can be unsubstituted or mono- or up to octasubstituted by the same or different substituents from the group of hydrogen, or Y;

a 1-, 2-, 3-, 4-, 5-, 6-, 7-, 8- or 9-phenanthridinyl radical, or a 1-, 2-, 3-, 4-, 5-, 6-, 7-, 8- or 9-phenanthridinyl-$C_{1-6}$ alkyl radical, wherein the $C_{1-6}$ alkyl radical can be unsubstituted or mono- or polysubstituted by the same or different substituents from the group of hydrogen, $C_{1-6}$ alkyl, halogen or oxo (=O), and the 1-, 2-, 3-, 4-, 5-, 6-, 7-, 8- or 9-phenanthridinyl radical can be unsubstituted or mono- or up to octasubstituted by Y;

a 2-, 3-, 4-, 5- or 6-pyridyl radical which can be unsubstituted or mono- or up to tetrasubstituted by the same or different substituents from the group of hydrogen, or Y;

a 2-, 3-, 4-, 5- or 6-pyridyl-$C_{1-6}$ alkyl radical, wherein the $C_{1-6}$ alkyl radical can be unsubstituted or mono- or polysubstituted by the same or different substituents from the group consisting of $C_{1-6}$ alkyl, halogen or oxo (=O), and the 2-, 3-, 4-, 5- or 6-pyridinyl radical can be unsubstituted or mono- or up to tetrasubstituted by the same or different substituents from the group of hydrogen, or Y;

a 2-, 3-, 4- or 5-thienyl radical, or a 2-, 3-, 4- or 5-thienyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 2-, 3-, 4- or 5-thienyl radical can be unsubstituted or mono- to trisubstituted by the same or different substituents from the group of hydrogen, or Y;

a 2-, 4-, or 5-thiazolyl radical, or a 2-, 4-, or 5-thiazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 2-, 4-, or 5-thiazolyl radical can be unsubstituted or mono- or disubstituted by the same or different substituents from the group of hydrogen, or Y;

a 3-, 4-, or 5-isothiazolyl radical, or a 3-, 4-, or 5-isothiazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 3-, 4-, or 5-isothiazolyl radical can be unsubstituted or mono- or disubstituted by the same or different substituents from the group of hydrogen, or Y;

a 2-, 4-, 5-, 6-, or 7-benzothiazolyl radical, or a 2-, 4-, 5-, 6-, or 7-benzothiazolyl-$C_{1-6}$ alkyl radical, wherein the $C_1-C_6$ alkyl radical can be unsubstituted or mono- or polysubstituted by the same or different substituents from the group of $C_1-C_6$ alkyl, halogen or oxo (=O), and the 2-, 4-, 5-, 6-, or 7-benzothiazolyl radical can be unsubstituted or mono- to tetrasubstituted by the same or different substituents from the group of hydrogen, or a 1-, 2-, 4-, or 5-imidazolyl radical, or a 1-, 2-, 4-, or 5-imidazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 2-, 4-, or 5-imidazolyl radical can be unsubstituted or mono- or up to trisubstituted by the same or different substituents from the group of hydrogen, or Y;

a 1-, 3-, 4-, or 5-pyrazolyl radical or 1-, 3-, 4- or 5-pyrazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 3-, 4- or 5-pyrazolyl radical can be unsubstituted or mono- or up to trisubstituted by the same or different substituents from the group of hydrogen, or Y;

a 1-, 2-, 3-, 4-, or 5-pyrrolyl radical, or a 1-, 2-, 3-, 4-, or 5-pyrrolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 2-, 3-, 4- or 5-pyrrolyl radical can be unsubstituted or mono- or up to tetrasubstituted by the sane or different substituents from the group of hydrogen, or Y;

a 1-, 3-, or 5-[1.2.4]-triazolyl radical, or a 1-, 3-, or 5-[1.2.4]-triazolyl-$C_{1-6}$ alkyl radical, wherein the $C_{1-6}$ alkyl radical can be unsubstituted or mono- or polysubstituted by the same or different substituents from the group of hydrogen, $C_{1-6}$ alkyl, halogen or oxo (=O), and the 1-, 3-, or 5-[1.2.4]-triazolyl radical can be unsubstituted or mono- or disubstituted by Y;

a 1-, 4-, or 5-[1.2.3]-triazolyl radical or 1-, 4-, or a 5-[1.2.3]-triazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 4-, or 5-[1.2.3]-triazolyl radical can be unsubstituted or mono- or disubstituted by the same or different substituents from the group of hydrogen, or Y;

a 1- or 5-[1H]-tetrazolyl radical, or a 1-, or 5-[1H]-tetrazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, or Y;

a 2- or 5-[2H]-tetrazoyl radical, or a 2- or 5-[2H]-tetrazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 2- or 5-[2H]-tetrazolyl radical can be unsubstituted or substituted by hydrogen, or Y;

a 2-, 4-, or 6-[1.3.5]-triazinyl radical, or a 2-, 4-, or 6-[1.3.5]-triazinyl-$C_{1-6}$ alkyl radical, wherein the $C_{1-6}$ alkyl radical can be unsubstituted or mono- or polysubstituted by the same or different substituents from the group of hydrogen, $C_{1-6}$ alkyl, halogen or oxo (=O), and the 2-, 4-, or 6-[1.3.5]-triazinyl radical can be unsubstituted or mono- or disubstituted by the same or different substituents from the group of hydrogen, or Y;

a 2-, 4-, or 5-oxazolyl radical, or a 2-, 4-, or 5-oxazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 2-, 4-, or 5-oxazolyl radical can be unsubstituted or mono- or disubstituted by the same or different substituents from the group of hydrogen, or Y;

a 3-, 4-, or 5-isoxazolyl radical, or a 3-, 4-, or 5-isoxazolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 3-, 4-, or 5-isoxazolyl radical can be unsubstituted or mono- or disubstituted by the same or different substituents from the group of hydrogen, or Y;

a 1-, 2-, 3-, 4-, 5-, 6- or 7-indolyl radical, or a 1-, 2-, 3-, 4-, 5-, 6- or 7-indolyl-$C_{1-6}$ alkyl radical, wherein the $C_{1-6}$ alkyl radical can be unsubstituted or mono- or polysubstituted by the same or different substituents from the group of $C_{1-6}$ alkyl, halogen or oxo (=O), and the 1-, 2-, 3-, 4-, 5-, 6- or 7-indolyl radical can be unsubstituted or mono- or up to hexasubstituted by the same or different substituents from the group of hydrogen, or Y.

4. A compound of formula 1 of claim 3, wherein in $R_4$ said fluorine atoms are trifluoromethyl, and said $C_{1-8}$ alkoxy is methoxy or ethoxy.

5. A compound of formula 1 of claim 1 wherein R, $R_1$, $R_2$, and $R_3$, have the meanings given above, and $R_4$ is phenyl which is unsubstituted or substituted by one or up to five same or different $C_{1-6}$ alkoxy groups, where adjacent oxygen atoms can also be linked by $C_{1-2}$ alkylene groups.

6. A compound of formula 1 of claim 1, wherein R, $R_1$, $R_2$ and $R_3$ have the meanings given above, and $R_4$ is 3,5-dimethoxyphenyl.

7. A compound of formula 1 of claim 1, wherein $R_4$ has the meaning given above, and R, $R_1$, $R_2$, and $R_3$ are each a hydrogen atom.

8. A compound of formula 1 of claim 1, wherein R, $R_1$, $R_2$, $R_3$ are each a hydrogen atom, and $R_4$ is a 3,5-dimethoxyphenyl radical.

9. A compound of formula 1 of claim 1, wherein R is 2-Cl, $R_3$ is 6-Cl, $R_1$ and $R_2$ are each hydrogen, and $R_4$ is:

10. A compound of formula 1 of claim 1, wherein R is 2-Cl, $R_3$ is 6-Cl, $R_1$ and $R_2$ are each hydrogen, and $R_4$ is:

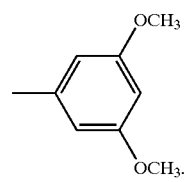

11. A compound of formula 1 of claim 1, wherein R is 2-Cl, $R_3$ is 6-Cl, $R_1$ and $R_2$ are each hydrogen, and $R_4$ is:

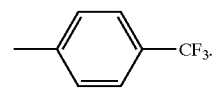

12. A compound of formula 1 of claim 1, wherein R is 2-Cl, $R_3$ is 6-Cl, $R_1$ and $R_2$ are each hydrogen, and $R_4$ is:

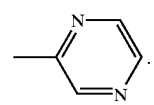

13. A compound of formula 1 of claim 1, wherein R is 2-Cl, $R_3$ is 6-Cl, $R_1$ and $R_2$ are each hydrogen, and $R_4$ is:

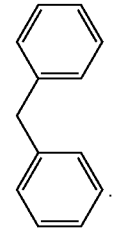

14. A compound of formula 1 of claim 1, wherein R is 2-Cl, $R_3$ is 6-Cl, $R_1$ and $R_2$ are each hydrogen, and $R_4$ is:

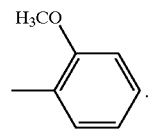

15. A compound of formula 1 of claim 1, wherein R is 2-Cl, $R_3$ is 6-Cl, $R_1$ and $R_2$ are each hydrogen, and $R_4$ is:

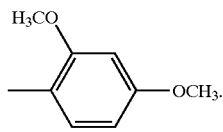

16. A compound of formula 1 of claim 1, wherein R is 2-Cl, $R_3$ is 6-Cl, $R_1$ and $R_2$ are each hydrogen, and $R_4$ is:

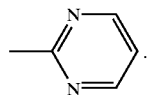

17. A compound of formula 1 of claim 1, wherein R is 2-Cl, $R_3$ is 6-Cl, $R_1$ and $R_2$ are each hydrogen, and $R_4$ is:

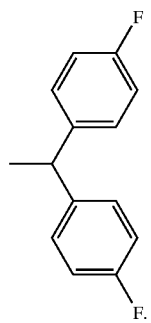

18. A compound of formula 1 of claim 1, wherein R is 2-Cl, $R_3$ is 6-Cl, $R_1$ and $R_2$ are each hydrogen, and $R_4$ is:

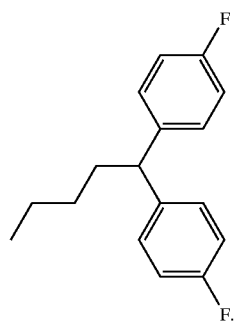

19. A compound of formula 1 of claim 1, wherein R is 2-Cl, $R_3$ is 6-Cl, $R_1$ and $R_2$ are each hydrogen, and $R_4$ is phenyl.

20. A compound of formula 1 of claim 1, wherein R is 2-Cl, $R_3$ is 6-Cl, $R_1$ and $R_2$ are each hydrogen, and $R_4$ is:

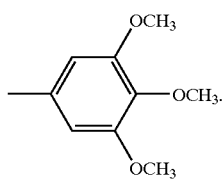

21. A compound of formula 1 of claim 1, wherein R is 2-Cl, $R_3$ is 6-Cl, $R_1$ and $R_2$ are each hydrogen, and $R_4$ is:

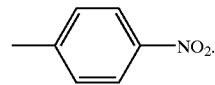

22. A compound of formula 1 of claim 1, wherein R is 2-Cl, $R_3$ is 6-Cl, $R_1$ and $R_2$ are each hydrogen, and $R_4$ is:

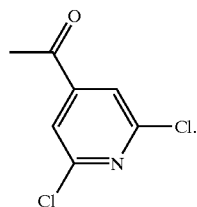

23. A compound of formula 1 of claim 1, wherein R is 2-Cl, $R_3$ is 6-Cl, $R_1$ and $R_2$ are each hydrogen, and $R_4$ is:

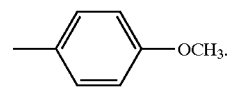

24. A compound of formula 1 of claim 1, wherein R is 2-Cl, $R_3$ is 6-Cl, $R_1$ and $R_2$ are each hydrogen, and $R_4$ is:

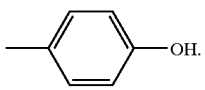

25. A compound of formula 1 of claim 1, wherein R is 2-Cl, $R_3$ is 6-Cl, $R_1$ and $R_2$ are each hydrogen, and $R_4$ is:

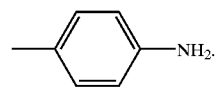

26. A compound of formula 1 of claim 1, wherein R is 2-Cl, $R_3$ is 6-Cl, $R_1$ and $R_2$ are each hydrogen, and $R_4$ is —COOEt.

27. A compound of formula 1 of claim 1, wherein R is 2-Cl, $R_3$ is 6-Cl, $R_1$ and $R_2$ are each hydrogen, and $R_4$ is:

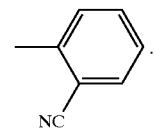

28. A compound of formula 1 of claim 1, wherein R is 2-Cl, $R_3$ is 6-Cl, $R_1$ and $R_2$ are each hydrogen, and $R_4$ is:

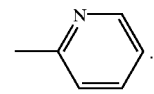

29. A compound of formula 1 of claim 1, wherein R is 2-Cl, $R_3$ is 6-Cl, $R_1$ and $R_2$ are each hydrogen, and $R_4$ is:

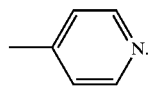

30. A compound of formula 1 of claim 1, wherein R is 2-Cl, $R_3$ is 6-Cl, $R_1$ and $R_2$ are each hydrogen, and $R_4$ is:

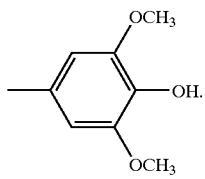

31. A compound of formula 1 of claim 1, wherein R is 2-Cl, $R_3$ is 6-Cl, $R_1$ and $R_2$ are each hydrogen, and $R_4$ is:

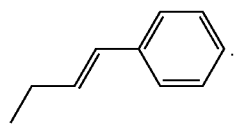

32. A compound of formula 1 of claim 1, wherein each of R, $R_1$, $R_2$ and $R_3$ are each hydrogen, and $R_4$ is:

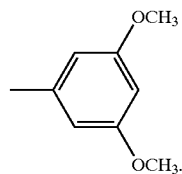

33. A compound of formula 1 of claim 1, each of R, $R_1$, $R_2$ and $R_3$ are each hydrogen, and $R_4$ is:

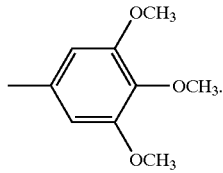

34. A compound of formula 1 of claim 1, each of R, $R_1$, $R_2$ and $R_3$ are each hydrogen, and $R_4$ is:

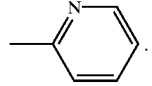

35. A compound of formula 1 of claim 1, wherein each of R, $R_1$, $R_2$ and $R_3$ are each hydrogen, and $R_4$ is:

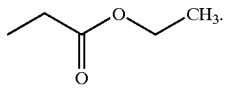

36. A compound of formula 1 of claim 1, wherein each of R, $R_1$, $R_2$ and $R_3$ are each hydrogen, and $R_4$ is:

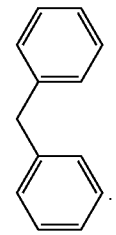

37. A compound of formula 1 of claim 1, wherein each of R, $R_1$, $R_2$ and $R_3$ are each hydrogen, and $R_4$ is:

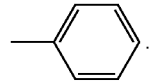

38. A compound of formula 1 of claim 1, wherein each of R, $R_1$, $R_2$ and $R_3$ are each hydrogen, and $R_4$ is:

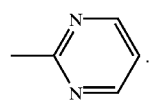

39. A compound of formula 1 of claim 1, wherein each of R, $R_1$, $R_2$ and $R_3$ are each hydrogen, and $R_4$ is:

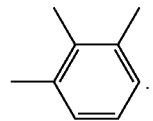

40. A compound of formula 1 of claim 1, wherein each of R, $R_1$, $R_2$ and $R_3$ are each hydrogen, and $R_4$ is:

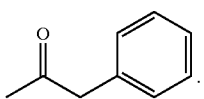

41. A compound of formula 1 of claim 1, wherein each of R, $R_1$, $R_2$ and $R_3$ are each hydrogen, and $R_4$ is:

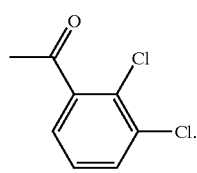

42. A compound of formula 1 of claim 1, wherein each of R, $R_1$, $R_2$ and $R_3$ are each hydrogen, and $R_4$ is:

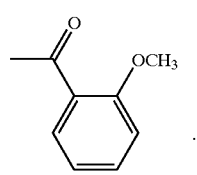

43. A compound of formula 1 of claim 1, wherein R is 2-OCH$_3$, R$_3$ is 6-OCH$_3$, R$_1$ and R$_2$ are each hydrogen, and R$_4$ is:

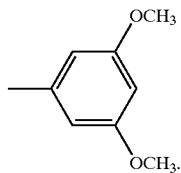

44. A process for preparing a compound of formula 1 of claim 1, which comprises reacting a pyridine carboxylic acid of formula (2)

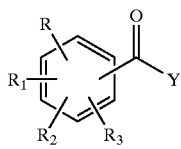

in which R, R$_1$, R$_2$, and R$_3$ have the meanings given in claim 1, and Y is a leaving group with an amine of formula (3)

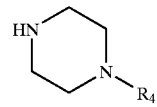

(3)

in which R$_4$ has the meanings given in claim 1, optionally in the presence of diluents and auxiliaries.

45. The process of claim 44, wherein said leaving group is halogen, hydroxyl, C$_{1-6}$ alkoxy, —O-tosyl, —O-mesyl, or imidazolyl.

46. The process of claim 45, wherein said C$_{1-6}$ alkoxy is methoxy or ethoxy.

47. A method for treating tumors in mammals effectively treatable therewith, which comprises administering to a mammal in need therefor an antitumor effective amount of at least one compound of formula 1 of claim 1.

48. A pharmaceutical composition comprising a compound of claim 1 as an active ingredient, optionally together with a conventional pharmaceutically acceptable auxiliary, additive and carrier.

* * * * *